United States Patent
Smith et al.

(10) Patent No.: US 6,891,606 B2
(45) Date of Patent: May 10, 2005

(54) REAL-TIME ON-LINE SENSING AND CONTROL OF MINERAL SCALE DEPOSITION FROM FORMATION FLUIDS

(75) Inventors: J. Kevyn Smith, Houston, TX (US); C. Mitch Means, Richmond, TX (US); Mingdong Yuan, Missouri City, TX (US); John L. Przybylinski, Missouri City, TX (US); Thomas H. Lopez, Houston, TX (US); Michael James Ponstingl, St. Louis, MO (US)

(73) Assignee: Baker Hughes Incorporated, Houston, TX (US)

( * ) Notice: Subject to any disclaimer, the term of this patent is extended or adjusted under 35 U.S.C. 154(b) by 89 days.

(21) Appl. No.: 09/975,161

(22) Filed: Oct. 11, 2001

(65) Prior Publication Data

US 2003/0071988 A1 Apr. 17, 2003

(51) Int. Cl.$^7$ .............................................. G01N 33/28
(52) U.S. Cl. ....................... 356/70; 356/128; 73/152.42
(58) Field of Search ........................ 356/70, 128–137; 250/255, 256, 269.1, 301; 73/152.42

(56) References Cited

U.S. PATENT DOCUMENTS

| | | | | |
|---|---|---|---|---|
| 3,945,439 A | | 3/1976 | Shupe et al. ................. 166/308 |
| 4,282,929 A | * | 8/1981 | Krajicek ..................... 166/303 |
| 4,916,317 A | | 4/1990 | Gabriel et al. .............. 250/341 |
| 5,353,237 A | | 10/1994 | Bass et al. .................. 364/502 |
| 5,396,325 A | | 3/1995 | Carome et al. ............. 356/128 |
| 5,734,098 A | | 3/1998 | Kraus et al. ............. 730/61.62 |
| 6,250,140 B1 | | 6/2001 | Kouznetsov et al. ........... 73/86 |
| RE37,283 E | | 7/2001 | Kluth et al. .................. 385/12 |
| 6,266,619 B1 | | 7/2001 | Thomas et al. ............... 702/13 |
| 6,268,911 B1 | | 7/2001 | Tubel et al. .................. 356/72 |
| 6,281,489 B1 | | 8/2001 | Tubel et al. ........... 250/227.14 |
| 6,388,251 B1 | * | 5/2002 | Papanyan ................ 250/269.1 |
| 6,501,072 B2 | * | 12/2002 | Mullins et al. ............. 250/256 |
| 6,690,453 B2 | * | 2/2004 | Mougin ....................... 356/70 |

FOREIGN PATENT DOCUMENTS

| | | |
|---|---|---|
| EP | 0442813 B1 | 4/1994 |
| EP | 1211540 A1 | 6/2002 |
| WO | WO91/03728 | 3/1991 |
| WO | WO01/29370 A1 | 4/2001 |

OTHER PUBLICATIONS

R. Philip–Chandy et al.; *A novel technique for on–line measurement of scaling using a multimode optical fibre sensor for industrial applications,* Sensors and Actuators B 71 (2000), pp. 19–23.

* cited by examiner

Primary Examiner—Richard A. Rosenberger
Assistant Examiner—Vincent P. Barth
(74) Attorney, Agent, or Firm—Madan, Mossman & Sriram, P.C.

(57) ABSTRACT

The present invention provides a method and system for controlling mineral scale deposition from a formation fluid. The rate at which scaling is occurring is measured in real time using an attenuated total reflectance probe and a photometer. The results are then used to determine whether to increase, decrease or leave unchanged addition of anti-scaling additives.

19 Claims, 4 Drawing Sheets

REAL-TIME ON-LINE SENSING AND CONTROL OF MINERAL SCALE DEPOSITION FROM FORMATION FLUIDS

BACKGROUND OF THE INVENTION

1. Field of the Invention

This invention relates to a method for use in oilfield and pipeline operations to monitor and control mineral scale precipitation from formation fluids. This invention particularly relates to a method for monitoring and controlling the deposition of mineral scale that is originating from formation fluids contained in wellbores, pipelines, and related equipment.

2. Background of the Art

Petroleum fluids primarily consist of oil and water and are herein referred to as formation fluids. A formation fluid may also contain oil and water insoluble compounds such as clay, silica, waxes, and asphaltenes, which exist as colloidal suspensions.

In addition to the already listed components, formation fluids can also include inorganic components which can precipitate to form mineral scales. The process of mineral scale precipitation is known as scaling. Of primary concern to this invention are mineral scales and scaling. The most common scale forming ions are calcium and barium, but sodium, carbonate, bicarbonate, chloride, sulfate, and strontium are also recognized as scaling species. The most common speciation of these combined scaling ions are: calcium carbonate ($CaCO_3$), calcium sulfate ($CaSO_4$), barium sulfate ($BaSO_4$), and strontium sulfate ($SrSO_4$). In addition, there are less common scale species, such as calcium fluoride ($CaF_2$), iron sulfide ($Fe_xS_{x+1}$), zinc sulfide (ZnS), lead sulfide (PbS) and sodium chloride (NaCl).

Scale precipitation is primarily affected by commingling of incompatible produced waters and/or changes in physical properties intrinsic to the well system such as, temperature, pressure, fluid turbulence, fluid flow rate, and pH. Specifically, well equipment in positions where incompatible water commingles and/or changes in these intrinsic physical properties occur is particularly vulnerable to scale precipitation. It has also been recognized that well equipment and topside equipment downstream of these sites are also susceptible to scale precipitation in the well system. Any mineral scale sticking to the well system surfaces may narrow pipes, and clog wellbore perforations, various flow valves, and other wellsite and downhole equipment, which results in wellsite equipment failures. It may also slow down, reduce or even totally prevent the flow of formation fluid into the wellbore and/or out of the wellhead. These effects also extend to crude oil storage facilities which incur maintenance or capacity problems when mineral scale precipitations remain undetected for extended periods of time.

As a result of these aforementioned problems, during oil production in production wells, the drilling of new wells, or workovers of existing wells, many chemicals, referred herein as "additives", which include scale inhibitors, are often injected from a surface source into the wells to treat the formation fluids flowing through such wells to prevent or control the precipitation mineral scale. In addition to controlling mineral scale precipitations, additives are also injected into producing wells to, among other things, enhance production through the wellbore, lubricate downhole equipment, or to control corrosion, and the formation or precipitation of asphaltenes, paraffins, emulsions and hydrates.

All of these chemicals or additives are usually injected through a conduit or tubing that is run from the surface to a known depth within the formation. Surface (topside) pipelines and equipment may also be protected by continuous injection or batch treatment of additives directly into the system, typically upstream of the problem location. In addition, an additive can be injected into a near wellbore formation via a technique commonly referred to as "squeeze" treatment, from which the additive can be slowly released into the formation fluid. Also, chemicals are introduced in connection with electrical submersible pumps, as shown for example in U.S. Pat. No. 4,582,131, or through an auxiliary line associated with a cable used with the electrical submersible pump, such as shown in U.S. Pat. No. 5,528,824.

In order to effectively inject additives into a formation fluid in order to control scaling, it is necessary to know how much of the additives are needed. At present, scaling tendency and scale occurrence are typically assessed by using an in-situ scale coupon or relying on water samples derived from production or injection sources. Off line field water samples are typically analyzed for ion concentrations either in the field or these samples are sent to an off-site laboratory wherein instrumental analysis is utilized to determine the relative concentrations of scaling ions contained in a given water sample. Again, another off-line approach to predicting and monitoring scale tendency and occurrence is the use of coupons which require their removal from the well system for inspection either in the field or at an off-site facility. Stated simply, there is a need for a real-time and in-situ monitoring technique for detecting the on-set of scale deposition in a production or injection system, where high pressure, turbulence and/or multiphase fluids may exist.

SUMMARY OF THE INVENTION

In one aspect, the present invention is a method for real time determination of mineral scale deposition from a formation fluid comprising: A) placing an optical probe in which the probe surface can measure changes in refractive index at the probe surface, into contact with a formation fluid produced or being produced from an oil well; B) measuring the changes in refractive index at the probe surface; and C) determining the on-set and rate, if any, of mineral scale deposition from the formation fluid as a function of the changes in refractive index at the probe surface; wherein: i) the probe surface which can be monitored for changes in refractive index is in contact with the formation fluid; ii) the probe, including the probe surface which can be monitored for changes in refractive index, is composed of a material which can withstand an extended period of contact with the formation fluid at the temperatures and pressures present in oil wells; and iii) the determination of the real-time scale deposition rate from the formation.

In another aspect, the present invention is a method for controlling mineral scale deposition from a formation fluid comprising: A) placing an optical probe having a probe surface which can measure changes in refractive index at the probe surface, into contact with a formation fluid produced or being produced from an oil well; B) measuring the changes in refractive index at the probe surface; C) determining the on-set and rate, if any, of mineral scale deposition from the formation fluid as a function of the changes in refractive index at the probe surface; D) comparing the rate, if any, of mineral scale deposition, to a predetermined range of acceptable mineral scale deposition; and E) effecting a change in the rate of addition, if any, to the formation fluid of an additive effective for preventing mineral scale deposition from a formation fluid; wherein: i) the probe surface which can be monitored for changes in refractive index is in contact with the formation fluid; ii) the probe, including the probe surface which can be monitored for changes in refractive index, is composed of a material which can withstand an extended period of contact with the formation fluid at the temperatures and pressures present in oil wells; iii) the determination of mineral scale deposition rate from the formation fluid takes place in real time; and iv) the rate of addition, if any, to the formation fluid of the additive effective for preventing mineral scale deposition from a formation fluid is: (1) increased when on-set of mineral scale deposition is detected or the mineral scale deposition rate is greater than the range of acceptable mineral scale deposition; (2) decreased when no mineral scale deposition is detected or the mineral scale deposition rate is less than the range of acceptable mineral scale deposition; and (3) unchanged when no mineral scale deposition is detected or the rate of mineral scale deposition is within the range of acceptable mineral scale deposition.

In yet another aspect, the present invention is a system for controlling mineral scale deposition from a formation fluid comprising a fluid flow path for flowing formation fluid recovered from a subsurface formation; an optical probe having a probe surface which can measure changes in refractive index at the probe surface, associated with the formation fluid in the fluid flow path providing data corresponding to the rate of deposition of mineral scale from the formation fluid in the fluid flow path; and a processor for determining from the data the rate of deposition of mineral scale from the formation fluid.

It would be desirable in the art of producing formation fluids and transporting it to refineries and/or disposal sites to be able to monitor scaling in an oil well, a pipeline, and related equipment if the monitoring could be done in real time and a cost efficient manner.

BRIEF DESCRIPTION OF THE DRAWINGS

For a detailed understanding and better appreciation of the present invention, reference should be made to the following detailed description of the invention and the preferred embodiments, taken in conjunction with the accompanying drawings.

DETAILED DESCRIPTION OF THE PREFERRED EMBODIMENT

Figure 1:
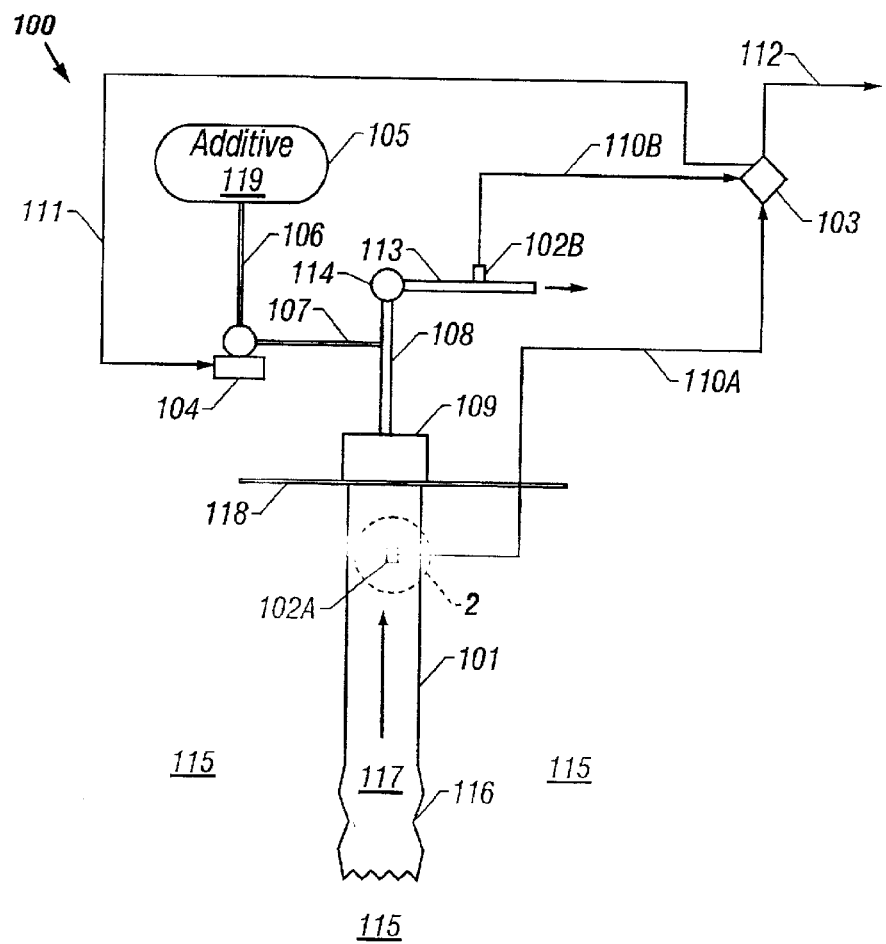
FIG. 1 is a schematic illustration of a wellsite system for monitoring the magnitude of scale occurrence reaching a wellhead and injecting chemicals in response to the monitored amounts according to one embodiment of the present invention.

The present invention relates to a system and method for monitoring and controlling scaling. The system may be used at a wellsite, a pipeline, and other places where formation fluid, oil or other complex mixtures subject to precipitating mineral scale are produced, transported, stored or used.

In the practice of the present invention, an optical probe having a probe surface which can measure changes in refractive index at the probe surface, is placed in contact with a formation fluid produced or being produced from an oil well. If the formation fluid in contact with the probe is precipitating mineral scale, some of the mineral scale will precipitate onto the probe surface. The scale on the probe surface results in a measured change in the refractive index at the probe surface.

In one embodiment of the present invention, a first measurement of change of refractive index at the probe surface is correlated with the magnitude of scale precipitation that is occurring in the fluid stream at the time of measurement. This real time measurement can then be used to make a first calculation regarding the quantity of scale inhibitor needed to reduce the scaling to an acceptable level. The calculation itself can be experimental or empirical and is preferably based on prior experience of the extent of scaling for the particular formation fluid being monitored.

In another embodiment of the present invention, the formation fluid is already being treated with a predetermined level of scale inhibitor and the resulting treated formation fluid has a measurable level of scaling. The change in refractive index at the probe surface is measured and compared to both a predetermined range and the previous measurements, if any. If there is no difference from the previous measurement or if the measurement is within a predetermined range, a signal or no signal is sent to a controller or controllers, which manages the level of scaling inhibitor treatments, to maintain the current or existing treatment rate.

If the difference in measurements is outside the predetermined range, it indicates that an undesirable amount of mineral scale either has or will be precipitated out of solution and become deposited somewhere in the wellbore, pipeline, transportation or storage facility as the case may be. This is undesirable, so in this case, a signal is sent by the controller or controllers to adjust the settings or rates in order to control, prevent, inhibit or otherwise mitigate scaling. The adjustments are made according to the nature and quantity of the difference. In most cases, additional additives are required to reduce or eliminate further scaling.

Another way of determining whether to make changes or adjustments of a treatment, such as a chemical injection, is to compare the measurements of change in refractive index at the probe surface in the flow path with a reference material. Preferably, the reference material is a sample of the reservoir fluids wherein the scaling is at an acceptable level.

Many different chemical, physical and spectroscopic ways of detecting and measuring scaling in formation fluid are utilized in the laboratory. Real-time or substantially real-time, on-site, scaling measurements are preferred and are thus provided in the present invention. For purposes of the present invention, on-site means in close proximity to the formation fluid being monitored with the methods of the present invention.

While any method known to those of ordinary skill in the art of making such measurements of scaling can be used with the present invention for determining acceptable ranges, reference materials and the like, the methods of the present invention are practiced using an optical probe having a probe surface which can measure changes in refractive index at the probe surface to detect the scaling of formation fluids. It is preferred to use a fiber optic probe, and particularly preferred to use an attenuated total reflectance probe, with a photometer to directly measure the amounts of scaling occurring in a formation fluid by measuring the refractance in a wavelength range of 400 nm to 1500 nm and then transmit the results to a data gathering and processing circuit or unit such as a microprocessor based unit or a computer for data analysis. Photometers useful with the present invention include single wavelength photometers, spectrophotometers, UV-VIS-NIR spectrophotometers, and the like. For the purposes of the present invention, the term ATR means an attenuated total reflectance device including a probe and a means of measuring the refractance of a material in contact with the probe.

An ATR is a preferred optical probe for the practice of the present invention because it is readily available and permits both in-laboratory measurements and real-time direct measurements of the absorbance of highly opaque or colored fluid or liquid within a process. Formation fluids, such as crude oil, are normally opaque and dark. ATR probes useful with the present invention can be placed at different locations in the flow paths of the formation fluid to collect scaling data, whether in a wellbore, in a pipeline or in other transfer lines. It is necessary that the probe be capable of withstanding the conditions downhole in an oil well. For example, ATR probes having sapphire windows are particularly preferred for use with the present invention.

Also a preferred optical probe for use with the present invention are ATR probes having a special geometry to augment sensitivity to changes in refractive index due to the deposition of scale on the surface of the probe. Trapezoidal in shape, the ATR probe surface is placed at the end of the probe which contacts the formation fluid. The surfaces of the trapezodial ATR probe tip that are exposed to the formation fluid are the top and angled sides. The base of the trapezodal ATR probe tip is attached to the probe body. Light emerging from the source at the opposite end of the detector is directed through the ATR probe.

The readings of the absorbance spectra of a typical formation fluid, such as a well stream, are made at a wavelength ranging from 400 nm to 1500 nm, commonly referred to as the visible and infrared spectral region. For the present invention, one preferred wavelength range is from 400 nm to 1500 nm. More preferably, the wavelength range is from 630 nm to 900 nm, and most preferably from 650 nm to 670 nm. A second preferred wavelength range is from 800 nm to 900 nm, preferably from 850 nm to 900 nm, and most preferably from 870 nm to 890 nm.

In the practice of the present invention, a sample is analyzed with an ATR wherein light, a form of electromagnetic wave, from a source is sent to a sensor with an exposed surface placed in contact with the formation fluid wherein the refracted light is sent back to the detector. Within the return trajectory back to the detector, filters may be placed to eliminate or isolate unnecessary light resulting from formation fluid fluorescence, phosphorescence, or reflectance. With proper connections and the associated instruments and electronics, the signals of a measured refractance resulting from a change in the refractive index at the surface of the sensor may be transmitted conveniently by using optical fibers to a control unit for spectral data storage, analysis and/or comparisons. The refracted light intensity obtained by using an ATR is analyzed and compared with the help of suitable computer programs or other processing unit. The path length may vary, depending on the wavelength of the light used.

It is important that the ATR probe be selected such that it can be used in the application of the present invention. For example, in a wellbore, a probe can be exposed to corrosive conditions and high temperatures and/or pressures. The optics of the probe should be such that they will not decompose or become permanently occluded. For example, preferably, the optics of a probe useful with the present invention will be made of sapphire.

The refractance of the scaling from a formation fluid may be expressed in different ways. It can be determined at a single point at a selected wavelength, at a plurality of wavelengths within the range disclosed herein, as an entire spectrum between two wavelengths or a combination thereof.

For a system of the present invention, it is preferred that there are at least two probes for obtaining at least two direct ATR measurement signals. For example, in the case of a system of the present invention being used to monitor an oil well, at least one probe is placed in the flow of fluid recovered at the wellsite in a fluid flow path prior to collecting the formation fluid for processing or transportation. There is typically an on-site processor to handle the data. The data obtained from direct ATR measurements of scaling from the formation fluid entering the perforations of the wellbore, exiting the wellhead and in a fluid flow path are collected, analyzed and compared. The probe data is preferably processed at the wellsite to determine the extent of scaling in the formation fluid, which is compared to the expected amount.

The comparison of relative scaling can be accomplished by using a processor. The expected amount and rate of scaling may be determined from analysis of prior fluid samples and/or modeling. If the amount of scaling in the formation fluid retrieved at the wellhead is greater than the expected amount, it can be reasonably inferred that scaling either is or will soon be occurring. Depending on the amount and rate of mineral scale precipitated, there may be a need to change or adjust various mitigating, controlling or inhibiting treatments such as injections of additives or, less preferably, changing temperatures or other conditions of the formation fluid. While any scaling is not desirable, there may be a range within which scaling can be tolerated.

For a system monitoring a pipeline transporting a formation fluid, it is preferred that there are also at least two ATR probes. It is preferred that at least one first probe is placed at a location to measure a first level of scaling upstream in the pipeline transportation system. It is also preferred that there is at least one second probe downstream from the first probe to measure a second level of scaling. It is within the scope of the present invention that a plurality of probes are used to monitor a long pipeline and/or its associated equipment in order to determine (a) if scale is occurring; (b) where scaling is occurring; (c) whether a treatment is needed or needs to be changed; and (d) what is a proper level of treatment.

As discussed hereinabove, there may be a plurality of probes for monitoring scaling in the same well or pipeline. It is also within the embodiment of the present invention to have a plurality of probes monitoring several wells or pipelines at the same time. The signals corresponding to refractance may be sent to the same or a different data processing unit, which compares the signals to determine if there exists a difference in scaling between that of the formation fluid entering the wellbore or pipeline and that at other places in the well or pipeline.

If there is no difference or the difference is small and within a predetermined range, commands are sent to one or more controllers maintaining the current treatment without any changes. If the difference is larger than the predetermined range, commands are sent to the controller or controllers to adjust their output or outputs for changing current treatments in accordance with the difference. Examples of treatments include injections of scale inhibiting additives, adjustment of the temperatures and pressures of pipes, valves and various other equipment, and combinations thereof.

There are other references that can be used to determine the extent of scaling in formation fluids. One such reference is a calculated figure. This figure may be obtained by methods such as a theoretical calculation, by extrapolation or interpolation of a calibration curve, and others. Another, and preferred reference is a laboratory analysis of the scaling in the actual fluid to be monitored. If it is difficult or not economic to place a probe downhole in the well, an intermittent sampling and analysis of the formation fluid in the wellbore is an acceptable reference of the present invention. It is also within the embodiment of the present invention to use a previous analysis from the same or a different monitoring system as a reference to determine the extent of scaling occurring in the subject formation fluid.

In the practice of the present invention, a predetermined range for a change in the relative scaling of a fluid is used to trigger or not trigger actions to control scale precipitation from a formation fluid. This predetermined range can be prescribed in many different ways or even a combination of ways because it depends upon the point at which scale will precipitate from a formation fluid which itself is subject to a number of factors. The factors which affect scale precipitation include the composition of the formation fluid, the scale causing compositions concentration in the particular formation fluid, the fluctuations of such compositions in the formation fluid, the equipment, the well history, the accuracy of the ATR used, the operating experience of a particular well or pipeline or storage facility, the effectiveness of a particular treatment for a well or a pipeline or a storage facility, and many other factors. Factors which may impact the accuracy of the ATR probe, include but are not limited to: homogeneity of the sapphire crystal matrix, detector quantum efficiency, light source bandwidth, and mode of beam splitting.

Because all the steps and measurements of the present invention do not need operator intervention, except for checking the accuracy of the sensors or probes, the present invention can be automated with proper computing devices, such as computers, signal transmitters and receivers, computational programs or software to perform the necessary calculations and data comparisons, and other necessary mechanical devices, which can be controlled non-manually when receiving various electromagnetic, electrical, electronic or mechanical commands, instructions or signals.

While the sensors or probes are used to provide direct real-time measurements of scaling, it is not required or needed that the measurements are made continuously. For the present invention, the sensors or probes may be operated in many different modes, continuous, semi-continuous, intermittent, batch or a combination thereof. Formation fluid composition and changes in the composition, operating experience and maintenance requirement are some of the factors that influence the choice of how often the measurements are made. Furthermore, it is also within the scope of the present invention that a different signal may be transmitted to a machine or computer or some other form of data processing unit, i.e., a processor, at a remote location and, in response to the difference observed, a decision of adjusting the output of an apparatus for a particular treatment is sent to that apparatus directly or back to the controller, which then sends a proper command to the apparatus.

One aspect of the methods of the present invention which is important to their practice is the fact that the probe surfaces being used to measure the rate of scaling will become occluded when scaling occurs. When this occlusion occurs, it is necessary to clean the probe surface. While such cleaning can be done manually, it is preferred that such cleaning take place automatically. If done automatically, automated systems such as the Welker® AID-1 system can be used and are preferably triggered by a controller monitoring the detector of the ATR probe. Cleaning can also be done on a schedule. In addition to cleaning, the device can also be used to calibrate, extract and insert the probe surface.

Whether the probes are cleaned manually or automatically, the removal of the scale can be done with appropriate reagents and solvents. For example, if the scale on the probe is primarily calcium carbonate, it can be removed using dilute acid. Any method known to those of ordinary skill in the art of cleaning scale from surfaces can be used with the methods of the present invention.

An additive to control or mitigate scaling is added to formation fluids in the practice of the present invention. Any additive known to those of ordinary skill in the art of treating production fluids to prevent scaling can be used with the present invention. Preferably, the additives used are: phosphate esters, phosphonates, poly maleic acid, poly acrylic acid, or other homo-, co- and ter-polymers, wherein these examples can be formulated at various proportions depending upon the application.

A step-by-step description of one embodiment in accordance with the present invention is made with reference to FIG. 1. FIG. 1 is a schematic diagram of a system (100) wherein scaling is monitored with two ATR probes (102 A&B). The first ATR probe (102A) is located in the wellbore (101) and the second ATR probe (102B) is located in a pipeline (113).

The system (100), in one aspect, is shown to include a wellbore (101) that extends to a producing zone (116). The formation fluid (117) from the producing formation (115), flows into the wellbore (101) and then flows upward to the surface (118). The formation fluid then passes through the wellhead (109) and then out through a well head header (108) to a pipeline junction (114), and then to a pipeline (113) or to other suitable transportation systems. The ATR probes (102A&B) are connected to data/power communication links (110A&B), which send signals to a wellsite controller (103).

The signals from the ATR probes (102A&B) are sent to the wellsite controller (processor) (103) which interacts with various programs and models. The wellsite controller (103) determines the extent of scale occurring in the production fluid (117) based on programs provided thereto. The extent of scaling is then compared to predetermined ranges. Based on these comparisons, the programs and models also determine if (a) they are different; (b) if the difference exceeds a predetermined range; and (c) how a treatment adjustment, if any, is needed in response to the difference.

If there is no difference or the difference does not exceed the predetermined range, then the controller does not make any adjustment or changes to the pump (104) speed providing additives (119) from a source (105). If the difference exceeds the range, the controller (103) changes the pump (104) speed using an active control line (111) to adjust the amount of the additive (119) to the desired amounts by increasing or decreasing the amount of additives (119) from the additive source (105) to suppress, control or mitigate the excessive scaling. The additives (119) are discharged into the well head header (108) via a supply line (107) after first being supplied to the pump (104) via a feed line (106).

All of the signals and/or instructions from computers or controllers may be communicated via conventional methods such as proper cables, optical fibers, etc. Alternatively, wireless communications are also within the embodiment of this invention. All of the measurements, comparisons and other operations may be automated with the help of proper devices. The system 100 may be a totally automated system. It is also possible to have manual intervention by an operator at the wellsite and/or at the remote location. Moreover, where a remote-controller or processor or second controller or processor (not shown) is used, the programs and models which reside in the same or different computing systems, can be used as a reciprocal backup operation. Communication with a second controller or processor can be accomplished using the remote data communications line (112).

It is optional to have a plurality of chemical sources and the respective pumps and metering devices to administer different additives or chemicals or solvents. These can be controlled individually or in concert with one another by one or more controllers such as (103). It is also within the scope of the present invention to use the same or different wellsite (on-site) and/or remote controller processors to manage the operation of two or more wells at the same time.

Figure 2:
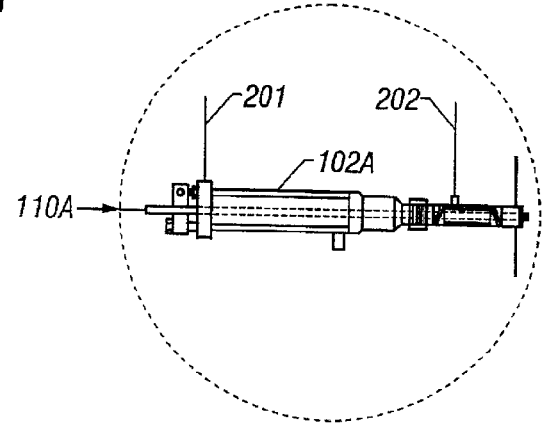
FIG. 2 is an expanded view of section A of FIG. 1.

FIG. 2 shows an alternative and preferred embodiment of the present invention wherein the system includes a device for cleaning the probe (102A). The probe (102A) is enclosed within an apparatus which withdraws the probe through the wall of a wellbore (101) and then cleans the probe, optionally using a cleaning agent from a source (not shown) delivered via a supply line (202) and then extends the probe back into the well bore and into contact with formation fluid. In another embodiment, a second device is used to clean the second probe (102B). Signals are sent from the probe using the data/power communication link (110A), and probe cleaning is activated using a data/power communication link (201).

It is further noted that while a part of the foregoing disclosure is directed to some preferred embodiments of the invention or embodiments depicted in the accompanying drawings, various modifications will be apparent to and appreciated by those skilled in the art. It is intended that all such variations within the scope and spirit of the claims be embraced by the foregoing disclosure.

EXAMPLES

The following examples are provided to illustrate the present invention. The examples are not intended to limit the scope of the present invention and they should not be so interpreted. Amounts are in weight parts or weight percentages unless otherwise indicated.

Example 1

A brine composition is divided into anion (AW) brine and cation (CW) brine where each brine contains only the respective scaling ions and sodium chloride. The pH of the AW portion of the brine is adjusted using glacial acetic acid to reach the desired point. CW water is mixed and used without further modification. All experimental data is generated at standard temperature and pressure conditions. The wavelength used for this experiment is 660 nm. Data is collected for both the probe and dynamic scale testing apparatus and is stored and analyzed at a sampling rate of 1 sample/sec.

Figure 3:
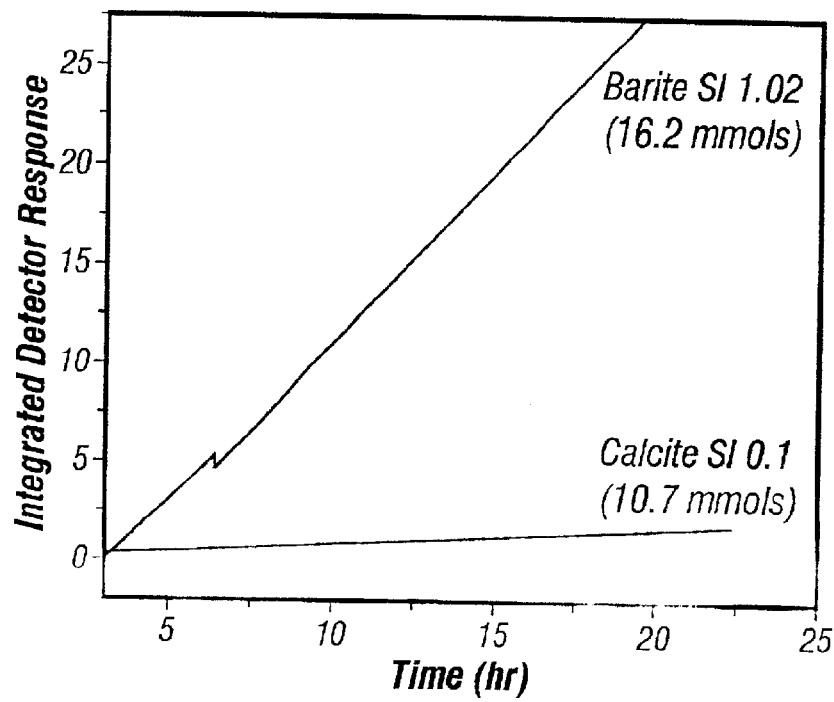
FIG. 3 represents the magnitude of detector response for brines that contain calcite or barite scaling ions.

FIG. 3 represents laboratory measurements utilizing a UV/Vis spectrophotometer and a fiber-optic ATR probe with de-ionized water as a reference. The scaling rate is determined for two unique brine solutions containing 16.2 mmol/L barium sulfate and 10.7 mmol/L calcium carbonate, respectively. These probe response differences shown in FIG. 3 reveal the sensitivity of the probe to different types of scale.

The scale sensor experimental apparatus consists of an open 2L beaker, which is placed upon a magnetic stirrer/heating mantel. The scale sensor is placed approximately one centimeter from the bottom and side of the beaker. CW is poured directly into the beaker and then data collection is initiated. Once data acquisition commences, AW is then added to the beaker.

The data is displayed in FIG. 3.

Example 2

Figure 4:
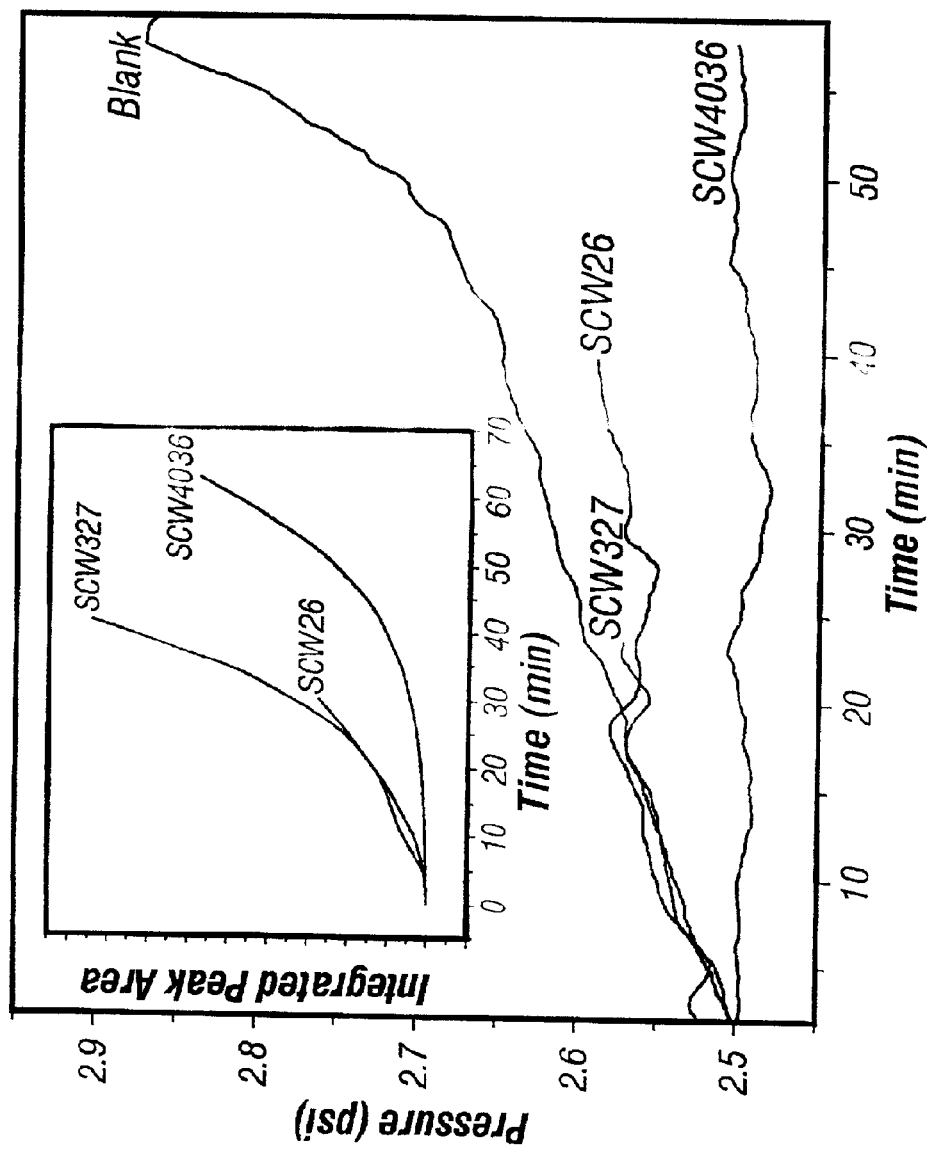
FIG. 4 demonstrates the correlation between the time dependent detector response (inset) and respective time dependent pressure increase resulting from scale deposition in a fluid stream where the brine has been treated with several scale inhibitors at the same concentration.

FIG. 4 demonstrates the correlation between the detector response rate and different scale inhibitor effectiveness for a given calcium carbonate scaling brine. These experiments correlate pressure increase in a flow loop with probe response are performed by coupling a dynamic scale testing apparatus with the probe.

Peristaltic pumps operating at a combined flow rate of 600 mls/hr, each individually pumped AW and CW through stainless steel tubing which is submerged in a water bath. In the water bath, both fluid lines (AW and CW) are combined and flowed through an $\frac{1}{16}$" (16 mm) OD stainless steel tubing whose ID was 1.6 mm and length was 1 m. A pressure transducer is located upstream from the AW and CW mixing point to measure the absolute pressure increase resulting from scale precipitation plugging the flow line. The probe is placed at the outlet of the tubing wherein the combined AW and CW are flowed over the probe tip. The scale inhibitors shown in FIG. 4 are commercial available from Baker Petrolite.

The data for both the pressure and the probe response is displayed in FIG. 4.

Example 3

Example 3 is performed substantially identically to Example 3 except that a single scale inhibitor is used at different concentrations.

Figure 5:
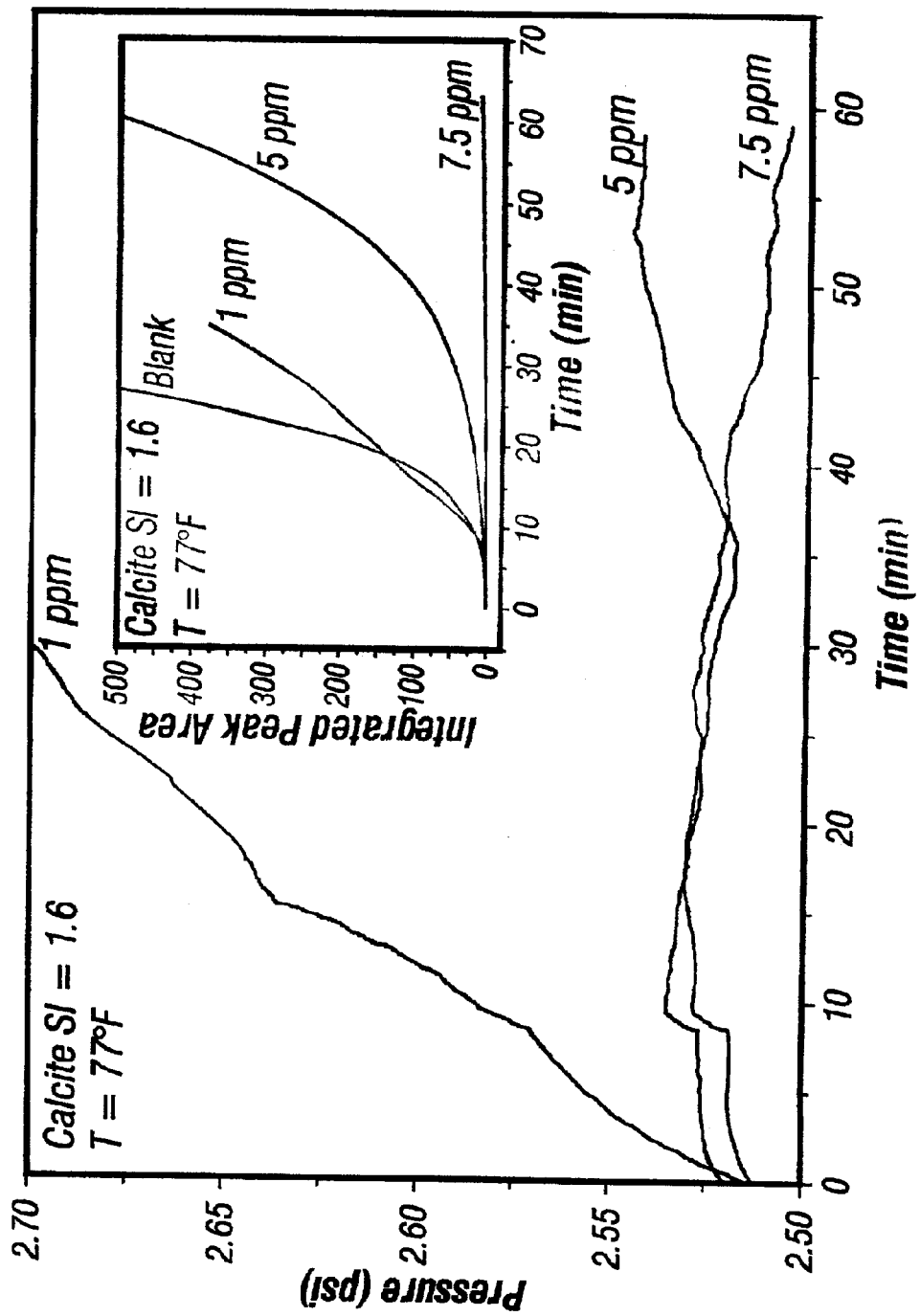
FIG. 5 further demonstrates the correlation between the time dependent detector response (inset) and respective pressure increase resulting from scale deposition in a fluid stream where the brine has been treated with several concentrations of the same inhibitor.

The data for both the pressure and the probe response is displayed in FIG. 5.

Example 4

Example 4 is performed substantially identically to Example 1 except that after the addition of the AW to the 2L beaker, crude oil is added to the solution. The crude is a sample from a well in the Gulf of Mexico and used without modification.

Figure 6:
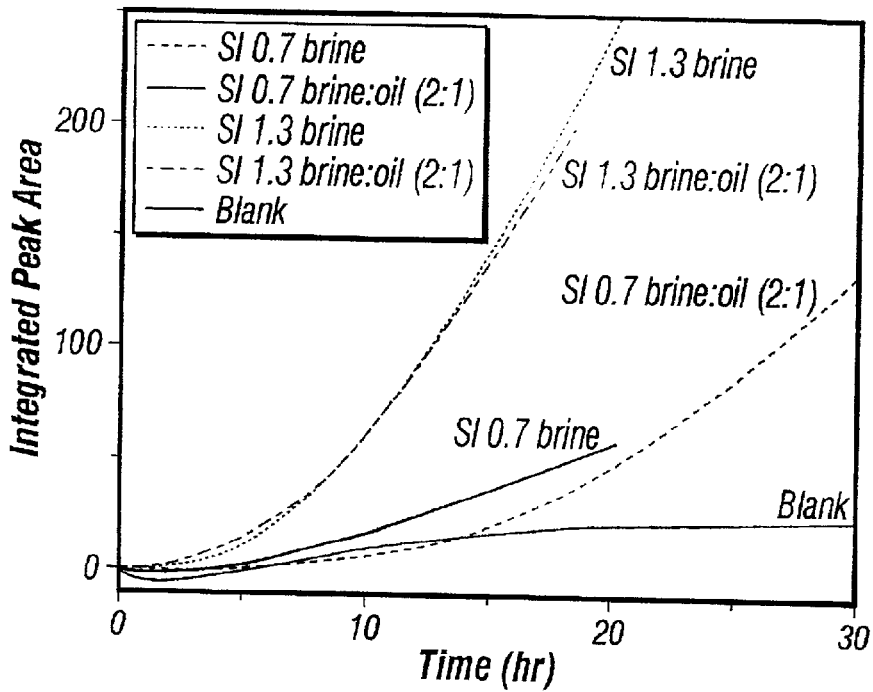
FIG. 6 demonstrates the selective monitoring capabilities of this invention to detect the on-set of different concentrations of calcite scale in mixed fluids (oil and water) similar to those found in the field.

The data is displayed in FIG. 6.

What is claimed is:

1. A method for real time determination the of mineral scale deposition rate from a formation fluid comprising:

A) placing an optical probe having a probe surface which can measure changes in refractive index at the probe surface, into contact with a formation fluid produced or being produced from an oil well;

B) measuring the changes in refractive index at the probe surface; and

C) determining the on-set and rate, if any, of mineral scale deposition from the formation fluid as a function of the changes in refractive index at the probe surface;

wherein:

i) the probe surface which can be monitored for changes in refractive index is in contact with the formation fluid;

ii) the probe, including the probe surface which can be monitored for changes in refractive index, is composed of a material which can withstand an extended period of contact with the formation fluid at the temperatures and pressures present in oil wells;

iii) the determination of on-set of mineral scale deposition and the mineral scale deposition rate from the formation fluid takes place in real time; and iv) the optical probe having a probe surface which can measure changes in refractive index at the probe surface is an ATR probe.

2. The method of claim 1 wherein the ATR probe includes a means of measuring the refractive index change associated with a material in contact with the probe which is a photometer.

3. The method of claim 2 wherein the photometer measures light in a wavelength range of from 400 to 1500 nanometers.

4. The method of claim 3 wherein the photometer measures light in a wavelength range of from 500 to 700 nanometers.

5. The method of claim 4 wherein the photometer measures light in a wavelength range of from 630 to 690 nanometers.

6. The method of claim 3 wherein the photometer measures light in a wavelength range of from 800 to 900 nanometers.

7. The method of claim 6 wherein the photometer measures light in a wavelength range of from 850 to 900 nanometers.

8. The method of claim 7 wherein the photometer measures light in a wavelength range of from 870 to 890 nanometers.

9. The method of claim 1 additionally comprising using an automated probe cleaning device to clean, calibrate, insert and extract the probe surface.

10. A method for controlling mineral scale deposition from a formation fluid comprising:

A) placing an optical probe having a probe surface which can measure changes in refractive index at the probe surface, into contact with a formation fluid produced or being produced from an oil well;

B) measuring the changes in refractive index at the probe surface;

C) determining the on-set and rate, if any, of mineral scale deposition from the formation fluid as a function of the changes in refractive index at the probe surface;

D) comparing the rate, if any, of mineral scale deposition, to a predetermined range of acceptable mineral scale deposition; and E) effecting a change in the rate of addition, if any, to the formation fluid of an of an additive effective for preventing mineral scale deposition from a formation;

wherein:

i) the probe surface which can be monitored for changes in refractive index is in contact with the formation fluid;

ii) the probe, including the probe surface which can be monitored for changes in refractive index, is composed of a material which can withstand an extended period of contact with the formation fluid at the temperatures and pressures present in oil wells;

iii) the determination of the mineral scale deposition rate from the formation fluid takes place in real time;

iv) the optical probe having a probe surface which can measure changes in refractive index at the probe surface is an ATR probe; and v) the rate of addition, if any, to the formation fluid of the additive effective for preventing mineral scale deposition from a formation fluid is:

(1) increased when on-set of mineral scale deposition is detected or the mineral scale deposition rate is greater than the range of acceptable mineral scale deposition;

(2) decreased when no mineral scale deposition is detected or the mineral scale deposition rate is less than the range of acceptable mineral scale deposition; and (3) unchanged when no mineral scale deposition is detected or the mineral scale race deposition is within the range of acceptable mineral scale deposition.

11. The method of claim 10 wherein the ATR probe includes a means of measuring the refractance of a material in contact with the probe which is a photometer.

12. The method of claim 11 wherein the photometer measures light in a wavelength range of from 400 to 1500 nanometers.

13. The method of claim 12 wherein the photometer measures light in a wavelength range of from 500 to 700 nanometers.

14. The method of claim 13 wherein the photometer measures light in a wavelength range of from 630 to 690 nanometers.

15. The method of claim 12 wherein the photometer measures light in a wavelength range of from 800 to 900 nanometers.

16. The method of claim 15 wherein the photometer measures light in a wavelength range of from 850 to 900 nanometers.

17. The method of claim 16 wherein the photometer measures light in a wavelength range of from 870 to 890 nanometers.

18. The method of claim 10 additionally comprising using an automated probe cleaning device to clean, calibrate, extract and insert the probe surface.

19. A system for controlling mineral scale deposition from a formation fluid comprising a fluid flow path for flowing formation fluid recovered from a subsurface formation; an ATR probe having a probe surface which can measure changes in refractive index at the probe surface, associated with the formation fluid in the fluid flow path providing data corresponding to the rate of deposition of mineral scale from the formation fluid in the fluid flow path; and a processor for determining from the data the rate of deposition of mineral scale from the formation fluid.

* * * * *